United States Patent [19]

Sarkisov et al.

[11] 4,368,191

[45] Jan. 11, 1983

[54] VACCINE AND METHOD PROPHYLAXIS AND TREATMENT OF TRICHOPHYTOSIS CAUSED BY PATHOGENIC ORGANISM TRICHOPHYTON MENTAGROPHTYES AND METHOD FOR PREPARING SAME

[76] Inventors: Arutjun K. Sarkisov, Begovaya alleya, 3, kv. 126; Lev I. Nikiforov, Semenovsky val, 12, kv. 46, both of Moscow, U.S.S.R.

[21] Appl. No.: 45,384

[22] Filed: Jun. 4, 1979

[30] Foreign Application Priority Data

Jun. 7, 1978 [SU] U.S.S.R. ............................... 2618901
Jun. 7, 1978 [SU] U.S.S.R. ............................... 2618902

[51] Int. Cl.$^3$ ............................................. A61K 39/00
[52] U.S. Cl. ....................................... 424/88; 435/254
[58] Field of Search ........................... 424/88; 435/254

*Primary Examiner*—Shep K. Rose
*Attorney, Agent, or Firm*—McAulay, Fields, Fisher, Goldstein & Nissen

[57] ABSTRACT

The vaccine for prophylaxis and treatment of trichopytosis caused by Trichophyton mentagrophytes comprises a suspension of microconidia of the immunogenic Trichophyton mentagrophytes strain No. 135/1963 in a physiological solution with a pH of 6.2–7.0 in an amount of 15–25 min microconidia per 1 ml of the physiological solution having 8–25 mln of viable microconidia.

A method for preparing the vaccine comprises growing the fungus culture Trichophyton mentagrophytes on a nutrient medium containing sources of carbon, nitrogen, biologically active compounds till an optimal accumulation of microconidia, separation of the resulting biomass, homogenization thereof to give a suspension of individual cells of the microorganism and drying of the resulting suspension.

A method for prophylaxis and treatment of trichophytosis caused by the pathologenic microorganism Trichophyton mentagrophytes comprising intramuscular injection of the vaccine to animals at the inner side of the thigh thereof in a dose of 1 to 4 ml twice at an interval of from 7 to 10 days.

11 Claims, No Drawings

VACCINE AND METHOD PROPHYLAXIS AND TREATMENT OF TRICHOPHYTOSIS CAUSED BY PATHOGENIC ORGANISM TRICHOPHYTON MENTAGROPHTYES AND METHOD FOR PREPARING SAME

BACKGROUND OF THE INVENTION

1. Field of the Invention

The present invention relates to veterinary and, more specifically, to a novel vaccine and method for prophylaxis and treatment of trichophytosis caused by a pathogenic organism *Trichophyton mentagrophytes* and a method for preparing same.

Dermatomycoses of animals and, in particular, trichophytosis of fur-bearing animals and rabbits are widely spread in all countries of the world. Trychophytosis endured by animals depreciates commercial qualities of fur products, hinders breeding jobs, breaks the plans for commercialization of animals and rabbit meat in commercial rabbit breeding. Ill animals comprise a constant threat and source of infection to the personnel and members of their families.

2. Description of the Prior Art

Among the currently employed preparations for the control of the disease the best known agent is griseofulvin which gives satisfactory results in treating dermatomycoses of fur-bearing animals and rabbits. However, taking into account that places of confinement of animals are infected with dermatomycosis agents and stability thereof in ambient medium, the animals in infected farms are under permanent threat of infection. In this connection, prophylaxis of the disease by means of griseofulvin can be effected only by way of a daily administration of the preparation during the entire period of life of the animals which is practically impossible to achieve. This results in considerable consumption of griseofulvin and makes this way of control of dermatomycosis economically inefficient.

The following references refer to publications related to the background of the invention.

1. A. H. Sarkisov, S. V. Petrovitch, L. I. Nikiforov, L. M. Yablochnik, V. P. Koroleva "Immunization of Cattle against Trichophytosis", J. "Veterinary", 1971, 2, 54–56 (in Russian).
2. USSR Inventor's Certificate No. 268593 for "Method of Specific Prophylaxis of Cattle Trichophytosis", 1970.
3. A. H. Sarkisov, L. I. Nikiforov, A. S. Pritula, S. V. Petrovich, H. A. Jilavijan "Dry vaccine LTF-130 against trichophytosis of cattle", VIEV Bulletin, 1976, XXV, pp. 7–10.
4. USSR Inventor's Certificate No. 348947 "Vaccine for Specific Prophylaxis and Therapy of Horse Trichophytosis", 1976.
5. V. P. Koroleva. Prevalence of Infectants of Dermatomycoses of Animals in Different Zones of the Country, VIEV Bulletin 1976, XXV, p. 49–52.
6. N. A. Spesivtzeva. "Mycoses and Mycotoxicoses", 1964.
7. G. G. Ainsworth, P. K. C. Austwick "Fungal Diseases of Animals" Comm. Agr. Bur. 1959.
8. C. J. Touche Trans St. John's Hospital, Derm. Sac., 1960, 45 19.
9. B. Chr. H. Gierloff, I. Katic, Nord. Vet.-Med., 1961, 13,571-92.
10. L. I. Nikiforov, "Infectants of Dermatomycoses of Fur mals and Rabbits", VIEV Bulletin, 1976, XXV, p. 75–75.

Observations and direct experiments performed with rabbits, silver foxes and polar foxes have shown that the animals which suffered from trichophytosis caused by *Trichophyton gypseum* as a result of a natural or experimental infection acquire immunity though commercial qualities of fur are lost and the focus of the disease is retained. This phenomenon has been taken into consideration in carrying out a program of investigations for the provision of a vaccine against trichophytosis of fur animals and rabbits.

Pathogenic fungi of the species *Trichophyton gypseum* (*T. mentagrophytes*) cause diseases in a wide range of animals including cage fur animals and rabbits, as well as in human beings and even birds, in contrast to the fungi of the species *T. verrucosum, T. equinum* and *T. gallinae* causing trichophytosis only with certain species of animals (See Table 2 hereinafter compiled according to the date published in 1 to 6.) This is explained, first of all, by high virulent properties of the strains of *Trichophyton gypseum*.

No effective preparations for the control of trichophytosis of fur animals and rabbits by way of a specific prophylaxis have been hitherto described in the literature.

The active preparations proposed first in the world practice for a specific prophylaxis of cattle, i.e. vaccine TF-130 and LTF-130/1-3/ and trichophytosis of horses /4/ cannot be used for treating trichophytosis of fur animals and rabbits caused by *Trichophyton gypseum* (*T. mentagrophytes*), since the animals immunized by these preparations acquire no immunity against the given kind of infection of trichophytosis. It is known that the injectant of the species *Trichophyton gypseum* causes disease in numerous species of animals including fur animals and rabbits, unlike the species *Trichophyton verrucosum, T. eguinum* and *T. gallinae* isolated mainly from animals of particular species and birds (see Table 1 compiled from the data of references 5 to 10 noted heretofore).

TABLE 1

| Man, species of animals, poultry | Trichophyton gypseum (mentagrophytes) | Trichophyton verrucosum | Trichophyton equinum | Trichophyton gallinae |
|---|---|---|---|---|
| Man | + | + | | |
| Cattle | + | + | | |
| Small cattle | + | + | | |
| Horse | + | | + | |
| Dog | + | | | |
| Silver fox | + | | | |
| Polar fox | + | | | |
| Chinchilla | + | | | |
| Rabbit | + | | | + |
| Poultry | | | | |

Our data /10/ obtained in studies performed with fur animals and rabbits ill with trychophytosis within the period of from 1963 to 1967 years also demonstrate that in 90% of cases of trichophytosis of fur animals and rabbits there is isolated *Trichophyton gypseum*.

Known in the art is a vaccine for prophylaxis of trichophytosis of cattle comprising a suspension of microconidia of the immunogenic strain *Trichophyton faviforme var. album* (*T. vericosum*) No. 130 in a physiological solution in a concentration of 6–9 mln in 1 ml of a sterile physiological solution.

The method for preparing this prior art vaccine resides in that the immunogenic culture *Trichophyton faviforme var. album* No. 130 is grown on a solid or liquid nutrient medium at a temperature of 26°–28° C. for a period of from 12 to 15 days until an optimal accumulation of microconidia of the culture is obtained, whereafter the biomass is separated, homogenized to give a suspension of individual cells of the microorganism and the desired product is isolated therefrom (cf. French Pat. No. 2,189,022; USSR Inventor's Certificate No. 3728641).

This prior art vaccine is employed only for prophylaxis of cattle trichophytosis and cannot be useful for prophylaxis and treatment of trichophytosis caused by pathogenic organisms of another species such as *Trichophyton mentagrophytes*.

Hitherto unknown are data on agents for a specific prophylaxis and treatment of triphophytosis caused by the pathogenic organism *Trichophyton mentagrophytes*.

Fur bearing animals are well known and conventional definitions can be found in Encyclopedia AMERICANA, Volume 12, available in the United States Patent and Trademark Office at least as early as Oct. 16, 1978 and Copyright 1978, available from the Americana Corporation, New York, N.Y. 10022, and Encyclopaedia Britannica, Volume 7, available in the United States Patent and Trademark Office since Apr. 12, 1974, Copyright 1974. In addition, publications such as Pictorial Encyclopedia of Furs, rev. ed (1950) by Authur Samet provides a comprehensive treatment of fur bearers and distinctions between fur-bearing mammals and non-fur bearing mammals.

As set forth in USSR patent application 2,618,902, a high virulence and contagiousness of *Trichophyton gypseum* in respect of human beings and numerous species of animals complicates research investigations on maintaining, attenuation and study of properties of this fungus, since the researcher per se has the risk of being infected with the disease (the course of treatment of the disease is rather complicated and lasting for 2–3 months) and spreading it among other people contacting him. The data relating to the preparation of strains of the fungus. *Trichophyton gypseum* possessing a lowered virulence with unchanged antigenous activity are hitherto unknown and non-described in the literature.

TABLE 2

| Man, species of animals | Trichophyton gypseum | Trichophyton verrucosum | Trichophyton equinum | Trichophyton gallinae |
|---|---|---|---|---|
| Man | + | + | | |
| Cattle | + | + | | |
| Small cattle | + | + | | |
| Horse | + | | + | |
| Dog | + | | | |
| Cat | + | | | |
| Polar fox | + | | | |
| Silver fox | + | + | | |
| Chinchilla | + | | | |
| Mice rodents | + | | | |
| Poultry | + | | | |
| Hen | | | | + |

Basic infectants of trichophytosis causing disease of human beings and animals

The purpose of the aforesaid invention was to provide a strain of *Trichophyton gypseum* (*T. mentagrophytes*) which would be harmless for human beings and animals with genetically stable characteristics, increased energy of growth on nutrient media which may be used for the development of antigenes, provision of a live vaccine and in scientific and commercial activities in premises of general labor conditions.

SUMMARY OF THE INVENTION

The starting strain was isolated in 1963 from a silver fox ill with trichophytosis at the farm of the sovkhoz "Somovsky", Voronezh region. As a result of the lasting investigations a strain has been obtained which possesses an increased energy of growth and better spore-formation, modified culture-morphological characteristics, substantially lowered virulent properties with unchanged antigenous structure and immunogenic activity.

The thus-obtained strain of the fungus is registered in the Collection of cultures of dermatophytes in the All-Union Institute of Experimental Veterinary under No. 135/1963.

The strain of the fungus *Trichophyton gypseum* No. 135/1963 has the following culture-morphological and biological characteristics:

the strain grows well on a wort-agar, Saburo glucose agar meat-peptone glucose agar. When inoculated as a suspension on wort-agar, at a pH value of from 5.6 to 7.0 and incubation at a temperature of from 24° to 28° C. for a period of from 8 to 14 days, it forms a solid strong thick whitish mycelium; at the 10–25-th day the mycelium becomes powder-like and has a yellowish color. When inoculated by injection into a flask, it forms a slightly protruding strong white colony which becomes powder-like and occupies the entire surface area of the medium by the 20–30-th day. On its other side the fungus gives a slightly red-brown pigmentation.

As it is seen from Table 3 hereinbelow, the strain *Trichophyton gypseum* No. 135/1963 according to the present invention differs from field strains by its weak virulence, absence of infection upon contact with animals; it does not cause diseases when injected into animals; it does not lower the quality of fur, and it possesses immunogenic character. The strain according to the present invention can be handled under both laboratory and industrial conditions without the risk of infection of the operating personnel.

Under laboratory conditions upon successive inoculations, passages on animals during the effect of elevated and low temperatures, sublimation drying, etc., the strain *Trichophyton gypseum* 135/1963 retained its properties since 1968 and does not reverse. The strain was administered by different methods (epicutaneously, intracutaneously, subscutaneously, intramuscularly, intravenously) to 68 animals and did not cause the disease with the pathology characteristic for virulent strains. There were no cases of infection of the personnel handling the vaccine strain during reinoculation, administration, control of injected animals and the like.

The strain *Trichophyton gypseum* No. 135/1963 can be used for the preparation of a vaccine against trichophytosis.

During the period of 1975–1977 subject to the laws in force in the USSR (under the approval of the General Directorate of Veterinary of the USSR Ministry of Agriculture dated March 10, 1976 No. 116-18 and Dec. 21, 1976 No. 116-15, etc.) tests of immunogenic properties of the strain according to the present invention were performed in a composition of a specially prepared vaccine, since the native mycellic mass of the fungus could not be used for practical immunization. The official aprobation effected on 87,400 silver foxes and polar foxes and 10,800 rabbits on farms with stable disease of trichophytosis has demonstrated high immunogenic properties of the vaccine produced on the basis of the strain according to the present invention as it is proven by the formal acts of the tests.

TABLE 3

| Strain Trichophyton gypseum No. 135/1963 | Strains T.Mentagrophytes field |
|---|---|
| 1. Virulence | |
| (a) Rubbing-in the culture into scarificated skin. Slightly virulent; separated desquamative regions only at the infection spot; self-curing (15-days); retaining high grades of fur skin products of the fur animals. | Highly-virulent; heavy deep injuries over the entire surface of the skin; secondary lesions; duration of the disease up to 90 days. The furskin products of the fur animals should be discarded; after special desinfection it satisfies the requirements of lower grades. |
| (b) Application to non-injured skin | |
| Application to non-injured skin causes no signs of the disease both with animals and with a man. | Application to a non-injured skin causes the formation of a trichophytic focus with a subsequent spreading over substantial areas of the animal body with injury of the skin hairs. The same with a man. |
| (c) Intramuscular administration | |
| Causes no infection of the contacting animals and men. A thin crust is formed at the injection spot which has a diameter of up to 10 mm; it passes over after 10-20 days. | Causes the formation of a trichophytic focus at the spot of the injection, secondary foci, generalized infection, infection of people upon the contact. |

References known to the applicants which may be pertinent to the subject matter of the invention and over which the vaccines according to the invention, methods for the preparation of the vaccines and methods for prophylaxis and treatment of trichophytosis in fur-bearing animals are as follows:

1. A. H. Sarkisov, S. V. Petrovitch, L. I. Nikiforov, L. M. Yablochnik, V. P. Koroleva "Immunization of Cattle against Trichophytosis", J. "Veterinary", 1971, 2, 54-56 (in Russian).
2. USSR Inventor's Certificate No. 268593 for "Method of Specific Prophylaxis of Cattle Trichophytosis", 1970.
3. A. H. Sarkisov, L. I. Nikiforov, A. S. Pritula, S. V. Petrovich, H. A. Jilavijan "Dry vaccine LTF-130 against trichophytosis of cattle", VIEV Bulletin, 1976, XXV, pp. 7-10.
4. USSR Inventor's Certificate No. 348947 "Vaccine for Specific Prophylaxis and Therapy of Horse Trichophytosis", 1976.
5. V. P. Koroleva. Prevalence of Infectants of Dermatomycoses of Animals in Different Zones of the Country, VIEV Bulletin, 1976, XXV, p. 49-52.
6. N. A. Spesivtzeva. "Mycoses and Mycotoxicoses", 1964.
7. G. G. Ainsworth, P. K. C. Austwick "Fungal Diseases of Animals" Comm. Agr. Bur. 1959.
8. C. J. Touche Trans St. John's Hospital, Derm. Sac., 1960, 45,19.
9. B. Chr. H. Gierloff, I. Katic, Nord. Vet.-Med., 1961, 13, 571-92.
10. L. I. Nikiforov, "Infectants of Dermatomycoses of Fur Animals and Rabbits", VIEV Bulletin, 1976, XXV, p. 74-75.

No effective preparations for the control of Trichophytosis of fur bearing animals and rabbits by way of a specific Prophylaxis have been hitherto described in the literature. The active preparations proposed for a specific prophylaxis of cattle and Trichophytosis of horses cannot be used for treating of Trichophytosis of fur bearing animals and rabbits caused by "Trichophyton Gyseum" (T. Mentagrophytes). The strain *Trichophyton Mentagrophytes* No. 135/1963 is on deposit in the culture collection of the All-Union Research Institute of Experimental Veterinary and Registered under No. 135/1963.

It is an object of the present invention to provide a vaccine for prophylaxis and treatment of trichophytosis caused by the pathogenic organism *Trichophyton mentagrophytes*.

This object is accomplished by the provision of a vaccine for prophylaxis and treatment of trichophytosis caused by the pathogenic organism *Trichophyton mentagrophytes* which, in accordance with the present invention, comprises a suspension of microconidia of the immunogenic strain No. 135/1963 of the species *Trichophyton mentagrophytes* in a physiological solution with a pH value of from 6.2 to 7.0 in an amount of from 15 to 25 mln in one ml of the physiological solution including 8-25 mln of viable microconidia.

DESCRIPTION OF THE PREFERRED EMBODIMENTS

To retain viability and immunogenic character of micronidia, the vaccine according to the present invention also contains a protective medium having the following composition, percent by weight:

| sorbitol | 10.0 to 40.0 |
|---|---|
| gelatine | 2.0 to 10.0 |
| water | the balance | in the amount of 1 ml of the protective medium per 600–1000 mln of microconidia.

The method for preparing the vaccine according to the present invention for prophylaxis and treatment of trichophytosis caused by the *Trichophyton mentagrophytes* involves growing the fungi on a nutrient medium containing sources of carbon, nitrogen, biologically active compounds to an optimal level of accumulation of microconidia, separation of the resulting biomass, homogenization thereof to give a suspension of individual cells of the microorganism, followed by drying the suspension to obtain the vaccine. In accordance with the present invention *Trichophyton mentagrophytes* which is grown on the nutrient medium at a temperature of 26°-28° C. for a period of from 15 to 30 days is used. To retain viability and immunogenic character of the microconidia, the resulting suspension of individual cells of the microorganism is mixed, prior to drying, with a protective medium having the following composition, percent by weight:

| sorbitol or saccharose | 10.0 to 40.0 |
|---|---|
| gelatine | 2.0 to 10.0 |
| water | the balance | at the rate of 1 ml of the protective medium per 1 ml of said suspension containing 600 to 1,000 mln of microconidia.

For the fungus culture, it is advisable to use the strain *Trichophyton mentagrophytes* No. 135/1963 obtained by the method of a multi-stage purposeful selection of the most rapidly growing fungus colonies with an abundant accumulation of oval-rounded microconidia. This new strain is deposited in the culture collection of the All-Union Research Institute of Experimental Veterinary and registered under No. 135/1963; it has the following morphological features and physiological properties.

Morphological features; The nature culture of a 20-25 days' age is characterized by numerous cluster-like microconidia, mycelium. Generally it comprises cluster like located on the side branches of mycelium oval having a rounded, and less frequently, rod-like microconidia 1.5-3.5 u in size. The mycelium thickness is 0.8 to 2.0 u. Helical coils of hyphae are absent. Rarely encountered are blunt macroconidia of 3-5 segments.

Cultural features; The strain is cultured on a wort-agar, and it also grows well on a Saburo and glucose agar, meat-peptone glucose agar. Spore suspension, when inoculated on the wort-agar (pH 5.6 to 7.0) and incubated at a temperature of from 24° to 28° C., forms a continuous strong white film within 5-8 days, and after 10-25 days the mycelium becomes powdery and acquires a yellow color. When inoculated by injection into a flask, it forms a slightly protruded strong colony of whitish color which occupies the entire surface of the medium after 20-30 days and gets a powdery appearance. The reverse color is pale red-brown.

Virulence

When applied to a scarificated skin of animals it causes desquamation of epidermis. Healing is observed after 15 days. There is no danger for the animals in contact with the inoculated ones; neither is it dangerous for infecting a man handling the strain or being in contact with the immunized animals.

Reactogenicity

Injection of the living culture in the animals causes no clinical signs of the disease or changes in the general condition: temperature rise at the injection site, swelling, increase of the body temperature. Rejection of food is not observed.

Antigenic properties

Serum titre of immunized animals is 1:320-1:1280 (agglutination test).

Immunogenic activity

*Trichophyton mentagrophytes* strain No. 135/1963 when administered to fur-bearing animals and rabbits for the purpose of immunization creates a strong immunity. Immunity in the inoculated animals is observed 20-25 days after the administration of the vaccine. The immunity duration is at least three years.

The method for preparing the vaccine according to the present invention is performed in the following manner.

The method consists in the following steps: preparation of a nutrient medium, inoculation of flat-bottomed flasks and culturing the fungus; preparation of the culture medium; removal and disintegration of the mycelium; mixing of the homogenate with a protective medium; dispensing to flasks; lyophilization of the material; sealing and labeling of the flasks; control of the vaccine.

Inoculation of the culture, removal and disintegration of mycelium; mixing the homogenate with the protective medium and dispensing into flasks, as well as sealing the flasks after drying are performed strictly obeying the requirements of sterility in special boxes equipped with a forced ventilation and supply of sterile air.

Wort-agar is used as the nutrient medium for culturing *Trichophyton mentagrophytes*. To prepare the wort-agar, a brewing non-finished wort with Turner's acidity of 1.9°-2.3° which is subjected to moist heat sterilization with flowing steam for 30 minutes a day for 3 days. The sterilized wort is stored for up to 30 days in a refrigerator at a temperature of from 2° to 8° C. The resulting brewing wort is diluted with water (tap water not alkaline) or distilled water up to 7-8% content of carbohydrates as indicated by Balling; then it is poured into a tank, pH prior to sterilization is adjusted at 7.8 to 8.2; afterwards, 2.5 to 3.0% of agar-agar is added, heated to dissolution of agar, filtered through a cotton-wool gauze filter and dispensed into sterile flasks. Sterilization is then carried out at 0.7 atm for 40 minutes. After sterilization, pH of the wort-agar should be 6.2 to 6.8. The flat culture flasks with the wort-agar after sterilization are kept for 3 days in a thermostat at the temperature of 26° and 37° C. for the purpose of checking the nutrient medium sterility, and then thoroughly inspected for purity.

The inoculum is prepared from the inoculation material, a 20-25 days' age culture (depending on the growth energy) of the commercial strain grown on the wort-agar in flat culture flasks is washed with a sterile physiological solution. The flat culture flasks with the wort-agar are inoculated at the rate of 5-7 ml of the fungal suspension per one flask. The inoculated flasks are placed in a thermostat and maintained at a temperature of 26°-28° C. for 20-25 days depending on the energy of growth and spore-formation. During the growth, the cultured flasks are regularly visually checked, starting with the second day, to detect any foreign contamination. In the case of bacterial or fungal contamination, the contaminated flasks are discarded.

To prepare the vaccine according to the present invention, the flasks with the nutrient medium are inoculated with the resulting inoculation material of the culture *Trichophyton mentagrophytes*. As the nutrient medium for growing the culture, use is made of wort-agar or another nutrient medium which can be used to ensure abundant growth of the mycelium and accumulation of microconidia without losing the immunogenic activity. The culture is incubated for 15 to 30 days at a temperature of 26°-28° C. On completion of growth, the fungal mass is removed and subjected to homogenization. The homogenization of the mycelium is effected in disintegrators ensuring a complete sterility during operation.

During the entire period of charging, disintegration and discharging the biomass, the temperature in the working chambers, wherein the biomass is disintegrated and circulated, as well as the temperature of homogenizers and colloidal mills of various types should not exceed 25° C. The disintegrators should be selected so that separation of microconidia from mycelium is ensured without damaging the microconidia.

On completion of homogenization the resulting homogenate is mixed with the protective medium.

As the protective medium (drying medium), use is made of a sterile aqueous solution containing 10 to 40% of saccharose or sorbitol and 2 to 10% of gelatine.

To prepare the protective medium, gelatine is added and placed into hot distilled water and then, after dissolution thereof, saccharose is introduced into the solution. The mixture is filtered, and the pH is adjusted from 7.0 to 7.4. The mass is subjected to a moist, heat sterilization. After sterilization, pH should be from 6.2 to 6.8.

Mixing of the homogenate with the protective medium is conducted at the rate of 1 ml of the protective medium per one ml of said suspension containing 600 to 1,000 mln of microconidia. After mixing, the resulting vaccine is dispensed into flasks and lyophilically dried. Each lot of the vaccine is tested for solubility, presence of foreign matter, residual moisture, absence of growth of foreign microflora and mould fungi; content of microconidia, content of live microconidia, innocuity, and immunogenic activity.

The vaccine is stored in a dry place at a temperature of from 2° to 6° C.

For a better understanding of the present invention, some specific example illustrating the assay of the vaccine and the method for preparing same are given hereinbelow.

EXAMPLE 1

Tests and application of the vaccine

The vaccine has been tested against trichophytosis of fur-bearing animals and rabbits.

The prepared experimental lots of the vaccine have been tested for purity and then, on 68 rabbits and 74 foxes and silver foxes, the harmlessness of the vaccine has been proven by way of intramuscular injection into a the animals in doses of from 0.2 to 0.4 ml/kg. No side effects have been observed.

The experiments have shown that the vaccine is harmless and non-reactogenic. When applied to the scarificated skin it causes a slight desquamation of epidermis which healed after 7-15 days. Intramuscular injection in doses of 3.5 and 10 ml per animal (fox, silver fox) results in no clinical signs of the disease or changes in the general condition. Increase of the local and general temperature, of food or other changes have not been observed. At the injection site, a thin crust with a diameter of 2-8 mm is formed after 10-15 days as a specific reaction to immunization which disappears spontaneously after 15 to 20 days.

In 42 rabbits tested, it has been found that the animals twice immunized with the tested lots of the vaccine are not susceptible to the experimental infection with virulent cultures and pathological material (pathogenic organism is *Trichophyton mentagrophytes*).

The infection is conducted by the conventional procedure 1-2 months after the second injection of the vaccine. In all cases, allergic phenomena have been observed in all immunized animals, namely, after 8-16 days desquamation in the inoculated area are of an epidermis, formation of separate thin greyish crusts which are completely sloughed after 20-25 days; intensive hair growth has been observed over the whole infected area. Mycological investigations have been negative. At the same time, the control animals (non-immunized rabbits) have shown a strong inflammation reaction after 15-25 days, painful palpation, formation of a thick solid crust in certain cases and the formation of secondary foci on the head has been observed. The duration of the infection process is up to 75 days. Retrocultures have been isolated. Fur coat is recovered 1-1.5 months after the disappearance of the clinical picture of the disease.

The test results are shown in Table 4 hereinbelow.

TABLE 4

| Group No. | Number of immunized animals | Experimental infective material | Number of diseased animals |
|---|---|---|---|
| 1 | 9 | culture | — |
| 2 | 9 | culture | — |
| 3 | 3 (control) | culture | 3 |
| 4 | 9 | pathological material | — |
| 5 | 9 | pathological material | — |
| 6 | 3 (control) | pathological material | 3 |

The obtained data on innocuity and immunogenic activity of the tested lots of the vaccine according to the present invention have made it possible to start experiments on fur-bearing animals. In a trichophytosis-infected animal breeding farm, a double immunization of 230 clinically healthy pups of foxes and silver foxes with a body weight of 2.5 to 3 kg was conducted for the purpose of prophylaxis. The vaccine has been injected intramuscularly in the dose of 1 ml at the inner side of thigh and the same dose is repeated 7 days later. The general condition of the animals has been satisfactory, no complications at the injection site have been observed. 7-12 days after the injection a thin crust with a diameter of up to 10 mm is observed which is then desquamated after 10-20 days. Observations during six months have shown that none of the vaccinated animals shows signs of trichophytosis, while during the same period at the farm there have been isolated 28 females and 344 pups with clinical signs of trichophytosis. 1.5 months after the immunization 5 vaccinated and 3 non-vaccinated (control) silver foxes have been subjected to an experimental infection. The three control animals show signs of trichophytosis, while the five vaccinated animals are resistant to the experimental infection.

Under field conditions the vaccine has been tested in animal breeding farms where trichophytosis occured for several years. In one of the farms, prior to the use of the vaccine according to the present invention, an antibiotic griseofulvin was employed for prophylaxis and therapentical purposes; disinfecting measures were taken, as well as treatment with medicinal preparations. However, the disease was recorded in these farms for more than five years with an increasing trend. In the year preceding the use of the vaccine according to the present invention, 229 animals of the main herd and 994 pups were showing symptoms of trichophytosis. As a preventive measure in this farm 17,294 animals were vaccinated. No complications were observed at the injection site. The general condition of the animals was satisfactory; off food, depression, decrease in reproduction, or fur quality were not observed. 105 pups with skin lesions manifested as separate hairless spots on their heads were isolated. The majority of the infected animals were revealed after the first administration of the vaccine. These animals recovered without any additional treatment. The next year at the same farm the whole population (13,998 animals) previously non-vaccinated were subjected to immunization. No cases of trichophytosis were observed. Similar results were obtained in the animal breeding farm where trichophytosis occurred for the first time with 36 females and 344 pups of foxes. The total immunization with the vaccine according to the present invention has made it possible to cure all the animals.

The results of the field observations with vaccination against trichophytosis of fur-bearing animals in five farms are shown in the following Table 5.

For the therapeutic purpose, the vaccine has been used under farm conditions in 185 foxes and silver foxes showing symptoms of trichophytosis with a different pattern of clinical signs of the disease. The vaccine has been injected twice intramuscularly at the inner side of the thigh, in a dose of 2–4 ml with an interval of 7 to 10 days. The curing effect was observed 15–35 days after the injectin without any additional treatment of the injected sites.

The vaccine has been used in infected animal breeding farms on the total population of over 211,000 silver foxes and foxes; the use of the vaccine according to the present invention has made it possible to eradicate the injection in the farms and keep a high quality standard of the fur products.

Large-scale testing of the vaccine according to the present invention under field conditions for treating trichophytosis of rabbits in productive farms with closed management system with the livestock population of 113,000 animals have shown that the use of the vaccine in constantly infected premises in combination with general sanitary and disinfection measures can result, within 3–4 months, in a total eradication of the disease.

Example 2

Preparation of one lot of the vaccine in the amount of 300,000 doses

Wort agar is used as a nutrient medium for culturing

TABLE 5

| | | *Trichophyton mentagrophytes* | | | | |
| | | Animals vaccinated | | Animals ill | | |
| No. | Animal variety | Total | Including ill ones | Within 1 month | After 1 month | Total, % | Efficiency, % |
|---|---|---|---|---|---|---|---|
| 1. | fox, silver fox | 25,898 | 36 | — | — | — | 100 |
| 2. | fox, silver fox | 37,473 | 23 | 96 | 9 | 0.2 | 99.8 |
| 3. | fox | 11,818 | 35 | 93 | 3 | 0.8 | 99.2 |
| 4. | fox, silver fox | 7,460 | 16 | 2 | 8 | 0.1 | 99.9 |
| 5. | fox | 4,838 | — | 5 | — | 0.1 | 99.9 |
| | TOTAL | 87,487 | 110 | 196 | 20 | 0.2 | 99.8 |

To this end, use is made of a brewing non-finished wort with a Turner's acidity of from 1.9° to 2.3° which is subjected to sterilization with flowing steam for 3 days, 30 minutes a day. The sterilized brewing wort is stored for 30 days in a refrigerator at a temperature within the range of from 2° to 6° C. The brewing wort is diluted with water to a Balling content of carbohydrates of 7–8%, pH is adjusted to 7.8 to 8.2 and the 2.5 to 3.0% of agar-agar is added and sterilized for 40 minutes under the pressure of 0.7 atm. After sterilization, pH of the wort-agar is equal to 6.2–6.8.

To prepare the inoculum, 150–200 and of saline solution is transfored into the original culture flask and then shaken carefully to wash off the growth 7–8 ml of the suspension and is withdrawn to inoculate each culturing flat flask of 1.5 l capacity. The inoculated flat flasks are placed into a thermostat in a half-inclined or horizontal position (with the nutrient medium upwards) and maintained at the temperature of 26°–28° C. After 5–8 days over the total surface of the medium a confluent layer of mycelial growth is formed which becomes powdery after 10–25 days and may acquire a yellow color. After 18–25 days the flasks are used for the preparation of the vaccine.

Te prepare the nutrient medium for culturing *Trichophyton mentagrophytes* strain No. 135/1963, the sterile nonfinished brewing wort is diluted with tap water to a 7–8% content of carbohydrates as indicated by Balling; 2.5–3% of microbiological agar-agar is added and dissolved upon heating, filtered and poured in 300 ml portions into the flasks. The latter are subjected to sterilization for 40 minutes under the pressure of 0.7 atm. 200 flat flasks are inoculated with *Trichophyton mentagrophytes* strain 135/1963. To inoculate this number of flasks 7 original culture flasks 20–30 days old are used. After 20–25 days the flasks with the grown culture are thoroughly visually observed and those with the slightest suspicion of contamination are discarded. 4.5 liters of the protective medium are prepared and checked for purity. To prepare the protective medium, into hot distilled water 4% (w/v) of food-grade gelatine is dissolved, then 20% w/v of sucrose is added the solution is filtered and its pH is adjusted to 7.0–7.4. The medium is sterilized for three days: the first day with flowing steam for 30 minutes, the second day and third day with flowing steam for 20 minutes and then for 40 minutes under the pressure of 0.7 atm. The harvested sample of the culture from 5 flasks is subjected to homogenization in 300 ml of sterile water, after which the number of microconidia is counted, whereafter the number of flasks with the culture required for disintegration is calculated so that the content of microconidia in the homogenate would be equal to 800 mln/ml. The culture is then harvested. This is done in sterile boxes, where the culture is removed by means of special scrapers from the surface of wort agar and placed in closed bottles. The harvesting of the growth is conducted carefully by touching the surface of the nutrient medium. Immediately after harvesting the growth it is thoroughly homogenized under strict sterility conditions. The temperature in the working chambers during homogenization should not exceed 30° C. To the homogenate the protective medium is added at the rate of 1 ml of the protective medium per one ml of the homogenate containing 600 to 1,000 mln of microconidia. The mixture is stirred and poured into flasks. The casettes with the flasks covered with two layers of gauze napkins are immediately placed into an ice-box chamber cooled to a temperature of −50° to −40° C. for a quick freezing. After 12–16 hours, well frozen flasks with the vaccine are rapidly transferred to a preconditioned and cooled chamber of a sublimation unit; the chamber is closed and vacuum pumps are switched on. After 1–3 hours the heating is also switched on to heat the chamber to a temperature of from 30° to 40° C. The heating is effected in such a manner that the temperature of the product would be increased by 1°–3° C. per hour; at the material temperature of 8°–10° C. the heating in the chamber is lowered to the temperature of 25° C. and maintained till the drying is completed. The temperature of the product should not exceed 25° C. The duration of drying varies from 90 to 96 hours. On completion of drying, the flasks are closed with corks and sealed. To check the quality characteristics of the vaccine 30 flasks are taken from each lot; 15 flasks are used for the quality control, the other 15 flasks are stored. The vaccine is checked for the following characteristics: appearance, presence of foreign matters, solubility, residual moisture, absence of contaminant, content and viability of microconidia, innocuity and immunogenic activity.

The resulting vaccine comprises a porous grey-brown dry mass in the form of a cylinder which, upon shaking, is detached from the flask walls.

To determine soluability, into five flasks with the vaccine there are introduced 5–10 ml of sterile water or physiological solution. The contents of the flask should be dissolved without residue within 2–3 minutes upon shaking.

To detect the impurities, the flask with the dissolved vaccine is observed by passing light. The flasks having foreign matters (fractions of glass, pieces of rubber sealings and the like) are discarded.

To determine the residual moisture, three portions are sampled, each of about 1 g (1–2 flasks) and kept in weighing beakers, then dried in a hot air oven at a temperature of from 100° to 105° C. for one hour. The residual moisture of the vaccine is 1 to 3.5%.

To detect the absence of growth of foreign microflora, five flasks with the dissolved vaccine are employed. From each flask inoculation is made, by means of a Pasteur pipette, transferring one or two drops into four test tubes containing meatpeptone agar, meat-peptone broth, Kitt-Tarozzi slant, Cvapek agar, wort agar. The test-tubes are separated into two groups (two test-tubes for each medium) and placed into thermostats at the temperature of 26° and 37° C. respectively for 10 days. The material inoculated onto the media of Kitt-Tarozzi and meat-peptone broth is re-inoculated on the fifth day onto the same media; besides, the material inoculum from the meat-peptone broth is re-inoculated onto meat-peptone agar and then again placed into the thermostat.

The material is clean, no growth of foreign microflora is observed.

The amount of microconidia is calculated for one milliliter of the vaccine dissolved in a solvent. A sterile physiological solution with pH of from 6.4 to 7.0 is used as a solvent. Microconidia are counted in the Goryaev's chamber and an average number is calculated from the data obtained from five flasks.

The content of microconidia is 15 to 25 min/ml.

The determination of the number of colony-forming microconidia is conducted in the following manner (the test is conducted with 5 flasks with the dissolved vaccine).

Into five test-tubes 4.5 ml of sterile water are poured by means of a pipette. The flasks with the vaccine is shaken; 0.5 ml is sampled therefrom by means of a pipette and transferred into the first test-tube. Then the contents thereof are stirred by means of a new pipette and transferred into the second test-tube, etc., i.e. serial dilution is made from $10^{-1}$ to $10^{-5}$. From the fifth test-tube portions of 0.5 ml are introduced into six Petri dishes containing wort-agar (with pH of from 6.3 to 6.8), and thoroughly spread over the surface. The Petri dishes are closed and placed into a thermostat at the temperature of 26° C. The number of the grown colonies is counted on the fifth day, using a meter for counting the number of colonies. The number of the grown colonies is totalized for six dishes and, by dividing this value by 3, the number of viable cells in 1 ml is obtained. This value multiplied by $10^5$ shows the number of viable microconidia. The number of viable micronconidia after drying is at least 8–10 mln per one ml of the ready-to-use vaccine.

Harmlessness of the vaccine is tested on rabbits injected intramuscularly into the thigh at the external side thereof. For each series of tests five rabbits are used with a mass of from 2.5 to 3 kg.

Observation of the animals is carried out for 10 days. The rabbits should remain alive. The vaccine series causing death of the animals or complications at the injection site as abscesses or tissue nectrosis should be repeateedly tested on a doubled number of animals. In the case of death or even one rabbit of presence of abscesses or necroses, the series is discarded and destroyed by autoclave treatment.

The immunogenic activity is tested on eight rabbits. Of these, five rabbits are twice injected with the vaccine in the dose of 1.0 ml. After 30 days five vaccinated and three control (non-vaccinated) animals are subjected to infection with a virulent culture of *Trichophyton mentagrophytes*. The infection is effected into a shaved area of 50×50 mm at the back skin between scapulae. The skin is rubbed with 70° ethanol and scarified with a shaving blade. 30 days old culture removed with agar from two test-tubes is ground and rubbed onto the scarified areas of eight rabbits by spatula.

Observations are carried out from 30 days. The immunized animals react to the infection by allergic signs at the application spot after 5–15 days in the form of separate regions covered with scales or a continuous crust. A strong inflammatory reaction is absent. Microscopy shows no damage of hairs or penetration of the fungus into the hair folliculae. Individual filaments of hyphae and small aggregates of the fungus arthrospores may be observed on hairs and dermal crusts. After 16–20 days the skin at the site of application of the virulent material is completely cleared from crusts and an intensive growth of hairs is observed within 25–30 days.

The control (non-immunized) animals show a strong exudative reaction with the formation of thick crusts after 8–15 days.

The clinical symptoms process lasts for 30 days or more, is characterized by an active penetration of the pathogenic organism into hair folliculae. Microscopic examination shows an abundance of fungal elements, i.e. spore chains and mycelium filaments around and in hairs, in the crusts.

Out of five immunized rabbits, four are not infected with trichopytosis, while three control animals show a typical pattern of the trichophytic process supported by the date of microscopic investigation.

To obtain a live dry vaccine against trichophytosis of fur animals and rabbits two mixtures of ingredients are prepared containing:

(1) a homogenate of a live culture of the fungus of the immunogenic strain Tr. mentagrophytes No. 135/1963 in sterile water with a content of 200 to 800 mln of live microconidia in one milliliter;

(2) a protective medium containing 10 to 40% of sorbitol or saccharose and 2 to 10% of gelatine dissolved in 100 ml of water and sterilized.

The mixture of said first and second components in a ratio of 0,5–1:0,5-1, after lyophilic drying, comprises a vaccine for a specific prophylaxis of trichophytosis of fur animals and rabbits.

The vaccine retaines its immunogenic activity and suitability for application for a period of at least one year when stored at a temperature of from +4° to 8° C.

The results of tests performed with the vaccine for prophylaxis of trichophytosis of fur animals in breeding farms:

TABLE 6

|   | Farm | Animal | Vaccinated total | Including ill animals | Taken ill Within the 1-st month | After 1 month | Total, % | Efficiency, % |
|---|---|---|---|---|---|---|---|---|
| 1. | "Audru", ESSR | fox, polar fox | 25,898 | 36 | — | — | — | 100 |
| 2. | "Kretingskoje" Lith. SSR | fox, polar fox | 37,473 | 23 | 96 | 9 | 0.2 | 99.8 |
| 3. | "Somovsky", Vorenezh region | fox | 18,818 | 35 | 93 | 3 | 0,8 | 99.2 |
| 4. | "Tobol' sky" Tiumen region | fox, polar fox | 7,460 | 16 | 2 | 8 | 0.1 | 99.9 |
| 5. | Experimental farm of the Research Institute NIIPZK, Moscow region | fox | 4,838 | — | 5 | — | 0.1 | 99,9 |
|   | TOTAL: |   | 87,487 | 110 | 196 | 20 | 0.2 | 99.8 |

The vaccine is used for preventive purposes, as well as for treating purposes for immunization of both young livestock and adult foxes, polar foxes and rabbits by way of a double, with intervals of 7 to 10 days, intramuscular injection at the inner thigh in the following prophylatic doses:

| young stock of silver foxes of a 1-4 months age | 1 ml |
|---|---|
| animals of older than 4 months and adult animals | 2 ml |
| rabbits after 45 days age | 1 ml. |

For the treating purposes the vaccine is administered in doubled doses following the same procedure.

After 10-15 days at the injection site there is observed the formation of a small (with a diameter of from 2 to 8 mm) trichiphytic-like spot which is a specific reaction for the injection which sponteously passes within 15-20 days.

The immunity of the vaccinized animals is developed after 20 days since the vaccination. The duration of immunity is at least two years.

According to the approval of the General Directorate of Veterinary of the USSR Ministry of Agriculture and the General Directorate of Veterinary of the RSFSR Minstry of Agriculture (See annexes) there were produced 437,000 doses of experimental lots of the vaccine which was tested on 87,400 foxes and polar foxes, 10,800 rabbits in five large fur animal-breeding farms and two rabbit farms with stationary unfavorable conditions as regards trichophytosis.

As a result of these large-scale investigations it has been found that the vaccine is harmless for human beings and animals, non-reactive, does not affect reproduction abilities, and creates with 99.2-99.9% of the vaccinized animals a strong tense immunity which makes it possible to ensure a specific prophylaxis of the disease. These characteristics of the vaccine are proven by the data shown in the following Table 6 and in Annexes.

Note in the above-mentioned fur-animals breeding farms over the years preceding to the mass vaccination with the vaccine of the present invention 10 to 40% of animals were taken ill with trichophytosis.

What is claimed is:

1. A vaccine for prophylaxis and treatment of trichophytosis in fur-bearing animals caused by the pathogenic organism Trichophyton mentagrophytes comprising:
   a suspension of microconidia of the strain No. 135/1963 of the Trichophyton mentagrophytes species in a physiological solution with a pH of from 6.2 to 7.0 in an amount of from 15 to 25 min of microconidia per 1 ml of the physiological solution including 8-25 million of viable microconidia.

2. A vaccine as claimed in claim 1, wherein
   a protective medium is contained for the protection of viability and immunogenic character of microconidia, and
   said protective medium has the following composition in percent by weight volume:

| sucrose or sorbitol | 10.0 to 40.0 |
|---|---|
| gelatine | 2.0 to 10.0 |
| water | the balance | in the amount of 1 ml of the protective medium per 600 to 1,000 mln of microconidia.

3. A method for prophylaxis and treatment of trichophytosis in fur-bearing animals caused by the pathogenic organism Trichophyton mentagrophytes using the vaccine of claim 1 or 2, comprising
   intramuscular injection of said vaccine to said fur-bearing animals in a dose of from 1-4 ml twice with an interval of from 7 to 10 days.

4. The method as claimed in claim 3, wherein
   the vaccine is injected at the inner side of the thigh of the fur-bearing animals.

5. A method for preparing a vaccine as claimed in claim 1 comprising:

culturing the fungus Trichophyton mentagrophytes on a nutrient medium containing sources of carbon, nitrogen, biologically active compounds at a temperature within the range of from 26° to 28° C. for a period of from 15 to 30 days until an optical accumulation of microconidia; separating of the resulting biomass; and homogenization thereof to give a suspension of individual cells of the microorganism followed by drying said suspension to obtain the vaccine.

6. A method as claimed in claim 5, wherein prior to drying, the resulting suspension of individual cells of the microorganism is mixed with a protective medium having the following composition, percent by weight:

| | |
|---|---|
| sorbitol or sacharaose | 10.0 to 40.0 |
| gelatine | 2.0 to 10.0 |
| water | the balance | at the rate of 1 ml of the protective medium per 1 ml of said suspension containing 600 to 1,000 mln microconidia.

7. A method as claimed in claim 5 or 6 wherein as the culture of the fungus use is made of the Trichophyton mentagrophytes strain No. 135/1963 produced by the method of multi-stage purposeful selection of rapid-growing fungus colonies with an abundant accumulation of oval-round microconidia.

8. A method for preparing a vaccine for prophylaxic and treatment of trichophytosis in fur-bearing animals comprising:

culturing the fungus Trichophyton mentagrophytes on a nutrient medium containing sources of biologically active compounds at a temperature within the range of from 26° to 28° C. for a period of from 15 to 30 days until an optical accumulation of microconidia;

separating the resulting biomass; and homogenization the resulting biomass to give a suspension of individual cells of the microorganism followed by drying said suspension to obtain the vaccine.

9. The method as claimed in claim 8 wherein prior to drying, the resulting suspension of individual cells of the microorganism is mixed with a protective medium having the following composition, percent by weight:

| | |
|---|---|
| sorbitol or sacharose | 10.0 to 40.0 |
| gelatine | 2.0 to 10.0 |
| water | the balance | as the rate of 1 ml of the protective medium per 1 ml of said suspension containing 600 to 1,000 mln microconidia.

10. The method as claimed in claim 8, wherein as the culture of the fungus use is made of the Trichophyton mentagrophytes strain No. 135/1963 produced by the method of multi-stage purposeful selection of rapid-growing fungus colonies with an abundant accumulation of oval-round microconidia which is deposited in the All-Union Institute of Experimental Veterinary and registered under No. 135/1963.

11. The method as claimed in claim 8, wherein the nutrient medium contains sources of carbon and nitrogen.

* * * * *